US009622778B2

(12) United States Patent
Wengreen et al.

(10) Patent No.: US 9,622,778 B2
(45) Date of Patent: Apr. 18, 2017

(54) SUBCUTANEOUS DELIVERY TOOL

(75) Inventors: Eric J. Wengreen, Blaine, MN (US);
John E. Lovins, Oakdale, MN (US);
Randy S. Roles, Elk River, MN (US);
Robert J. Nehls, Lakeville, MN (US)

(73) Assignee: Medtronic, Inc., Minneapolis, MN (US)

( * ) Notice: Subject to any disclaimer, the term of this patent is extended or adjusted under 35 U.S.C. 154(b) by 1083 days.

(21) Appl. No.: 12/250,670

(22) Filed: Oct. 14, 2008

(65) Prior Publication Data
US 2010/0094252 A1    Apr. 15, 2010

(51) Int. Cl.
| A61M 5/00 | (2006.01) |
| A61M 37/00 | (2006.01) |
| A61M 31/00 | (2006.01) |
| A61B 17/34 | (2006.01) |

(52) U.S. Cl.
CPC ..... *A61B 17/3468* (2013.01); *A61M 37/0069* (2013.01); *A61B 2017/3456* (2013.01); *A61M 37/00* (2013.01)

(58) Field of Classification Search
CPC ....... A61B 17/3468; A61B 2017/3456; A61M 37/00; A61M 37/0069; A61F 13/26
USPC .... 604/187, 93.01, 221, 181, 182, 500, 502, 604/507, 506, 218, 57–64; 600/578; 424/423
See application file for complete search history.

(56) References Cited

U.S. PATENT DOCUMENTS

| | | | |
|---|---|---|---|
| 4,636,202 A * | 1/1987 | Lowin et al. | 604/236 |
| 4,766,908 A * | 8/1988 | Clement | 600/578 |
| 4,871,094 A * | 10/1989 | Gall et al. | 222/386 |
| 5,279,555 A | 1/1994 | Lifshey | |
| 5,681,279 A * | 10/1997 | Roper et al. | 604/57 |
| 6,197,324 B1 * | 3/2001 | Crittenden | 424/423 |
| 6,436,068 B1 | 8/2002 | Bardy | |
| 6,786,883 B2 * | 9/2004 | Shippert | 604/15 |
| 6,939,318 B2 * | 9/2005 | Stenzel | 604/60 |
| 7,018,384 B2 | 3/2006 | Skakoon | |
| 2002/0147430 A1* | 10/2002 | Collins et al. | 604/218 |
| 2002/0188252 A1* | 12/2002 | Bardy | 604/93.01 |
| 2004/0204734 A1 | 10/2004 | Wagner et al. | |
| 2005/0165347 A1 | 7/2005 | Bardy | |

(Continued)

FOREIGN PATENT DOCUMENTS

EP    1 878 396 A1    1/2008

OTHER PUBLICATIONS

Medtronic Reveal® Plus Insertable Loop Recorder Product Overview, UC200701155 EN © Medtronic, Inc. 2006, Printed in USA, Oct. 2006.

(Continued)

*Primary Examiner* — Rebecca E Eisenberg
(74) *Attorney, Agent, or Firm* — Carol F. Barry

(57) ABSTRACT

Exemplary embodiments provide subcutaneous implantation tools and methods of implanting a subcutaneous micro-device using the same. Exemplary embodiments provide subcutaneous implantation tools including a syringe body, a dissection body, and a delivery assembly. Additional exemplary embodiments provide methods of implanting a subcutaneous micro-device, including inserting the dissection body of the tool described by the exemplary embodiments into an implantation site, where the dissection body includes a micro-device, and delivering the micro-device.

36 Claims, 16 Drawing Sheets

(56) References Cited

U.S. PATENT DOCUMENTS

2006/0253065 A1* 11/2006 Bardy ........................ 604/60
2007/0249992 A1    10/2007 Bardy

OTHER PUBLICATIONS

Medtronic Reveal® Plus Insertable Loop Recorder (ILR), © Medtronic, Inc. 2008, http://www.medtronic.corn/physician/reveal/index.html, printed on Jul. 8, 2008.
(PCT/US2009/060412) PCT Notification of Transmittal of the International Search Report and the Written Opinion of the International Searching Authority.

* cited by examiner

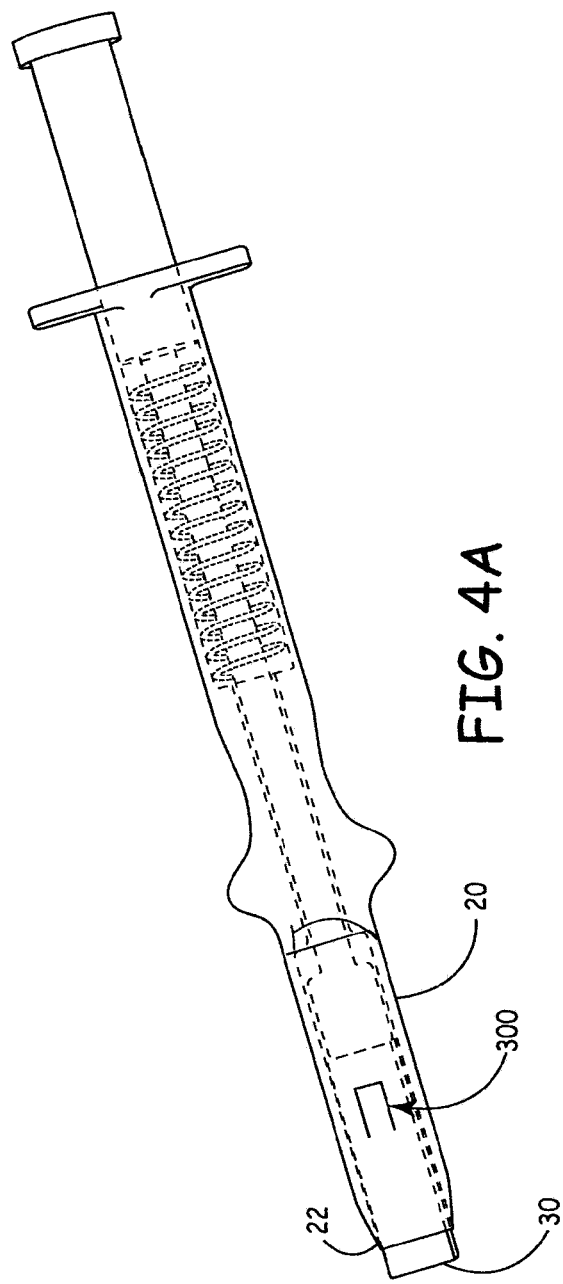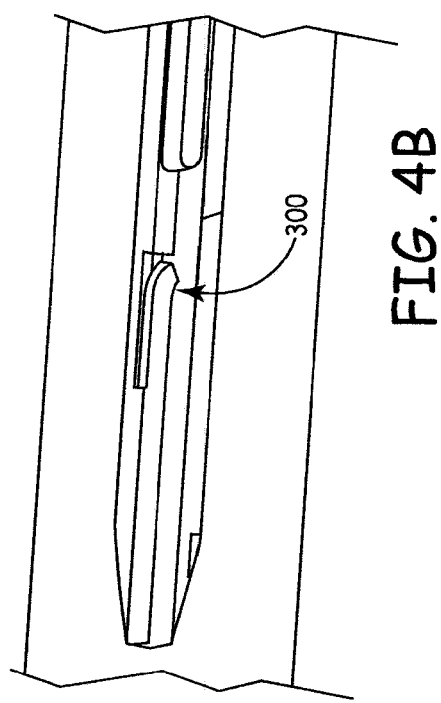
FIG. 4A
FIG. 4B

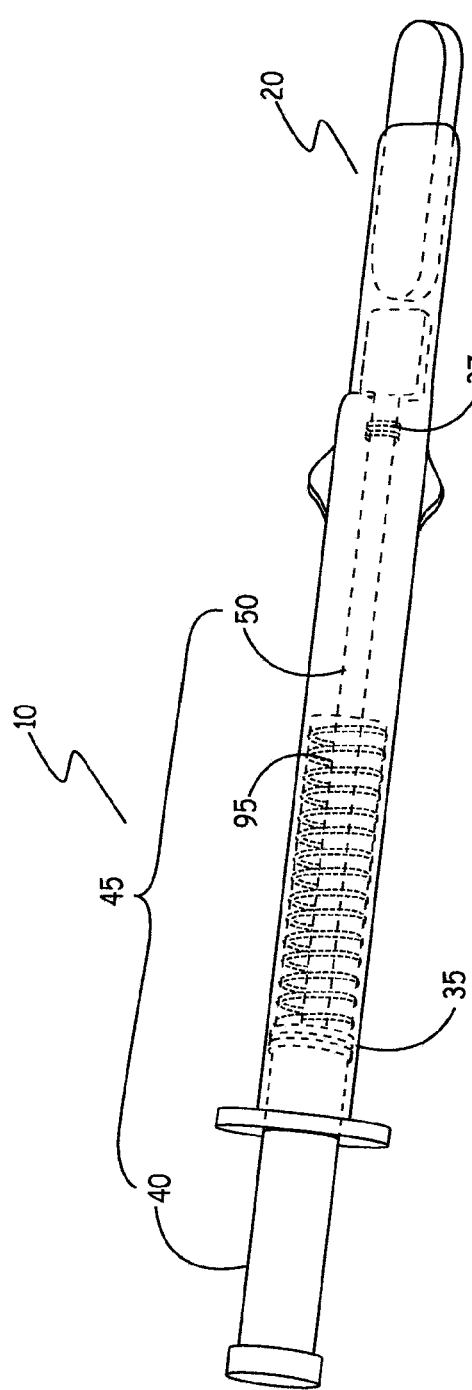
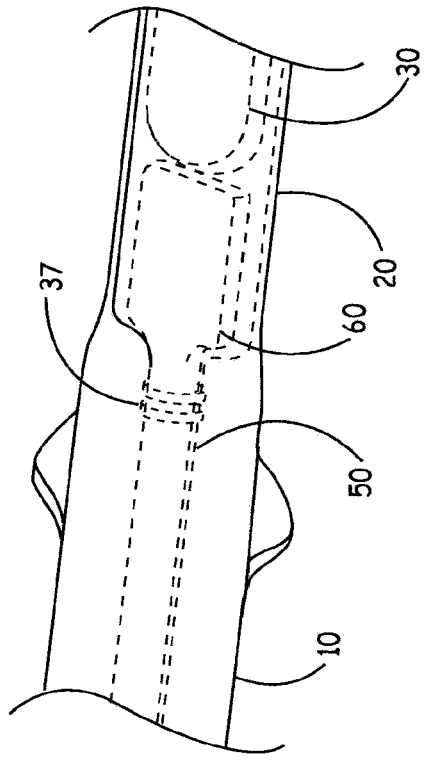
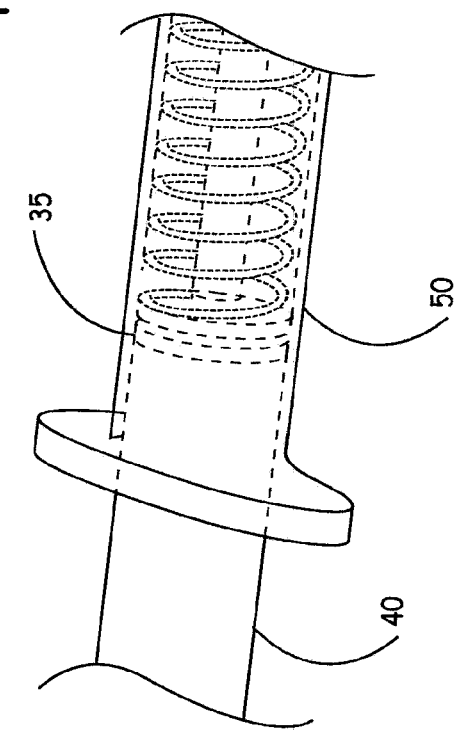
FIG. 7A
FIG. 7C
FIG. 7B

SUBCUTANEOUS DELIVERY TOOL

BACKGROUND

The use of monitoring equipment to measure various physical parameters of a patient is well known. There is a growing demand for using subcutaneous monitoring devices, which allow doctors to obtain information without a patient being connected to an external machine and/or which may otherwise not be reproducible in office settings. The term subcutaneous generally implies locations within the body of a patient under the skin. For example, an implantable device that includes the ability to monitor a patient's heart beat in order to detect transient symptoms suggesting cardiac arrhythmia would allow doctors to review data over a longer period of time than using external monitoring equipment in a simulated testing situation. However, to successfully implant implantable subcutaneous devices an implantation tool should, for example, ensure that the device is not implanted in muscle, reduce contact between the surgeon and the wound, be used in an office setting to minimize patient discomfort and the need for invasive surgery, have the ability to repeatedly recreate the same size incision site in the patient, and have the ability to implant differently shaped devices.

SUMMARY

Further areas of applicability will become apparent from the description provided herein. It should be understood that the description and specific examples are intended for purposes of illustration only and are not intended to limit the scope of the present disclosure.

Exemplary embodiments provide subcutaneous implantation tools and methods of implanting a subcutaneous micro-device using the same. Exemplary embodiments provide subcutaneous implantation tools including a syringe body, a dissection body, and a delivery assembly. The syringe body may have a substantially circular hollow bore extending along a longitudinal axis but is not limited to this shape. The dissection body may be attached at a distal end of the syringe body having a substantially non-circular hollow bore extending along the longitudinal axis and configured to receive a subcutaneous implantation micro-device. Further the delivery assembly may include a plunger fitting within at least a portion of the syringe body bore and a first end piece attached to a distal end of the plunger, where the plunger includes first and second portions. The first portion may have a substantially circular body, but is not limited to this shape, and the second portion may attach to a distal end of the first portion where the second portion is narrower than the first portion. The subcutaneous implantation tools may also include a fluid reservoir, a spring, a motion limiting assembly, and/or a micro-device.

Additional embodiments provide methods of implanting a subcutaneous micro-device, including inserting the dissection body of the tool described by the embodiments of the tool into an implantation site, where the dissection body includes a micro-device, and delivering the micro-device.

BRIEF DESCRIPTION OF THE DRAWINGS

Exemplary embodiments will be more clearly understood from the following detailed description taken in conjunction with the accompanying drawings. FIGS. 1-10 represent non-limiting, example embodiments as described herein.

FIG. 2 illustrates the syringe body and the dissection body of an implantation tool according to exemplary embodiments;

FIGS. 3 illustrate micro-devices including a tail;

FIG. 4A and 4B illustrate exemplary embodiments of an implantation tool including a friction-fitted micro-device;

FIG. 6 illustrates an implantation tool with blunt leading edges according to exemplary embodiments;

FIGS. 7A-7C illustrate exemplary embodiments of an implantation tool including a fluid reservoir;

FIG. 8 illustrates various exemplary embodiments of the implantation tool;

FIG. 10 is a flow chart illustrating a method of delivering a micro-device to a subcutaneous site according to exemplary embodiments.

DETAILED DESCRIPTION

Figure 1A:
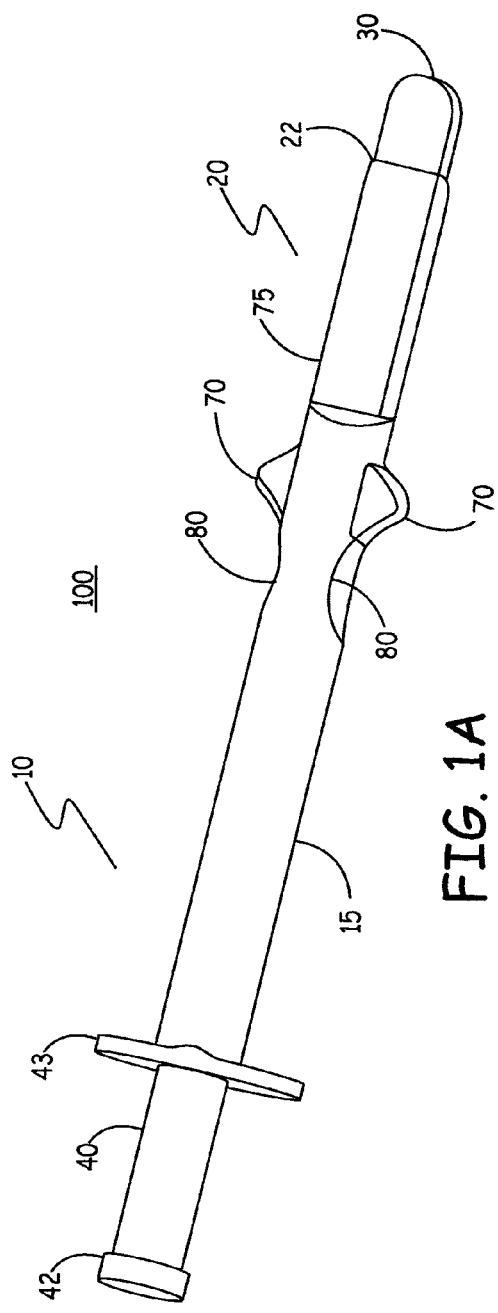
FIGS. 1A and 1B illustrate an external and internal view of an implantation tool according to exemplary embodiments.

Various exemplary embodiments will now be described more fully with reference to the accompanying drawings in which some exemplary embodiments are illustrated. In the drawings, the thicknesses of layers and regions may be exaggerated for clarity.

Accordingly, while exemplary embodiments are capable of various modifications and alternative forms, embodiments thereof are shown by way of example in the drawings and will herein be described in detail. It should be understood, however, that there is no intent to limit exemplary embodiments to the particular forms disclosed, but on the contrary, exemplary embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of exemplary embodiments. As used herein, the term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing only particular embodiments and is not intended to be limiting of exemplary embodiments. As used herein, the singular forms "a," "an" and "the" are intended to include the plural forms as well, unless the context clearly indicates otherwise. It will be further understood that the terms "comprises," "comprising," "includes" and/or "including,"

when used herein, specify the presence of stated features, integers, steps, operations, elements and/or components, but do not preclude the presence or addition of one or more other features, integers, steps, operations, elements, components and/or groups thereof.

Spatially relative terms, e.g., "beneath," "below," "lower," "above," "upper" and the like, may be used herein for ease of description to describe one element or a relationship between a feature and another element or feature as illustrated in the figures. It will be understood that the spatially relative terms are intended to encompass different orientations of the device in use or operation in addition to the orientation depicted in the Figures. For example, if the device in the figures is turned over, elements described as "below" or "beneath" other elements or features would then be oriented "above" the other elements or features. Thus, for example, the term "below" can encompass both an orientation which is above as well as below. The device may be otherwise oriented (rotated 90 degrees or viewed or referenced at other orientations) and the spatially relative descriptors used herein should be interpreted accordingly.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which exemplary embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Exemplary embodiments are directed to subcutaneous implantation tools and methods of implanting subcutaneous micro-devices. FIGS. 1A to 10 illustrate various exemplary embodiments of such subcutaneous implantation tools.

Figure 1B:
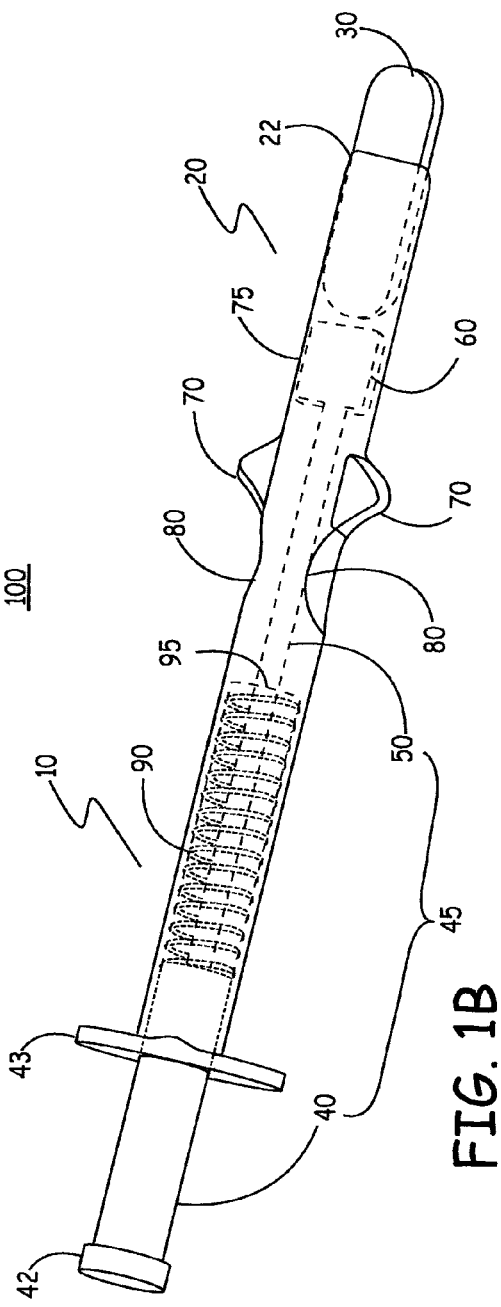
Figure 2:
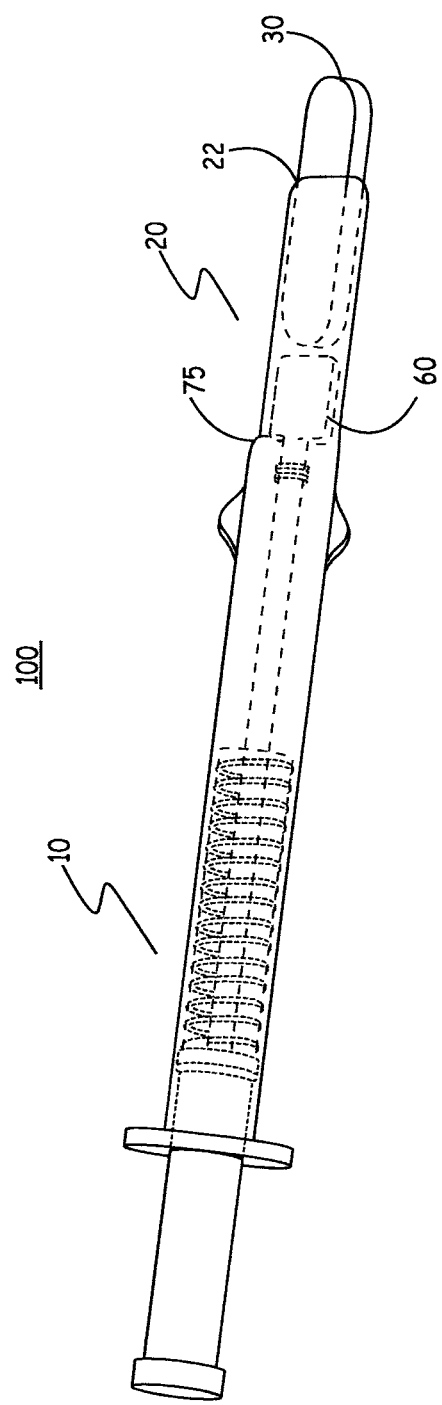

As shown in FIGS. 1A to 2, the subcutaneous implantation tool 100 includes a syringe body 10 and a dissection body 20. The subcutaneous implantation tool 100 also includes a delivery assembly including a plunger 45 having a first portion and a second portion 40 and 50 respectively, and an end piece 60. The micro-device 30 fits into dissection body 20 as shown. The micro-device 30 is implantable in biological bodies, e.g., human, animal (e.g., dog, cat, etc.), etc.

The syringe body 10 has a hollow bore 15 extending along a longitudinal axis. The syringe body 10 may include various configurations, for example, different lengths, widths, thicknesses, and shapes (e.g., substantially circular as shown). As shown in FIG. 1A, the syringe body 10 may have a scooped shape 80 at a distal end of circular bore 15 along which two fingers may hold the subcutaneous implantation tool 100 while a thumb may extend to the top of the plunger 45 to further secure the tool 100. Element 70 may also be used to further differentiate between the syringe body 10 and the dissection body 20 and to add a comfortable and ergonomic feel to the tool 100. The shape of element 70 may include, e.g., wings (shown), various shaped protrusions, etc. The element 70 may be integrally formed with the syringe body 10 and the dissection body 20 (e.g., molded plastic) or may be added at a later time.

The dissection body 20 has a substantially non-circular hollow bore extending along the same longitudinal axis as the syringe body 10. The dissection body 20 is located at a distal end of the syringe body 10 and may be integrally formed therewith. Also, the dissection body 20 is configured to receive a subcutaneous implantation micro-device 30. Although the subcutaneous implantation micro-device 30 is shown partially extending from the dissection body 20, the subcutaneous implantation micro-device 30 may also be located entirely within the dissection body 20. The dissection body may also include leading edges 22, which may be blunt.

The delivery assembly includes a plunger 45 having a first portion 40 and a second portion 50. The first portion 40 may have a substantially circular body that fits within at least a portion of the syringe body 15, but this shape is not intended to be limiting. The second portion 50 attaches to a distal end of the first portion 40 and may be narrower than the first portion 40 and have various shapes (e.g., circular, oval, flat, etc.). The second portion 50 fits in at least a portion of the syringe body 10 and the dissection body 20. In addition, the plunger 45 may form a watertight seal within the syringe body using, e.g., o-rings, etc.

The delivery assembly also includes an end piece 60 attached to a distal end of the plunger 45 that fits into at least a portion of the dissection body 20. The end piece 60 is used to deliver a micro-device 30 to a subcutaneous implantation site, as will be described below.

The delivery assembly may be integrally formed. Various medical grade materials may be used to form the various parts of the subcutaneous implantation tool 100, for example, plastics, metals, rubber, sanitizable materials, etc. Exemplary embodiments of the subcutaneous implantation tool 100 may be inexpensive, disposable, etc. The subcutaneous implantation tool 100 may also be configured to be used with known automated injection systems, which use, e.g., compressed air or other inert gases in place of a manual plunger.

The subcutaneous implantation tool 100 may also include a spring 90, which may be formed from medical grade metal. The spring 90 may be attached to a distal end of the plunger's first portion 40 and fitted within the syringe body 10. The spring 90 may also surround at least a portion of the plunger's second portion. The spring 90 exerts tension and/or pressure on the plunger's first portion 40 in order to initially maintain a predetermined distance between the end piece 60 and the distal end of the dissection body 20. By compressing the spring 90, the micro-device 30 is delivered and/or released, as will be described below.

In addition, a stopper 42 limits the distance that the micro-device 30 may be implanted by stopping the syringe body from moving along the longitudinal axis. For example, the stopper 42 is located at a proximal end of the plunger's first portion 40 outside the syringe body 10. The stopper 42 may be an end piece fitted onto the plunger's first portion 40 or may be integrally formed with the plunger 45. The stopper 41 may include various configurations, e.g., a circular cap that is wider than the syringe body 10 (as shown), a collar, etc.

As shown in FIG. 2, a limiting mechanism 75 may be used to differentiate between the syringe body 10 and the dissection body 20. The limiting mechanism 75 is located at a distal end of the syringe body 10 and prevents the subcutaneous implantation tool 100 from being inserted too far into the implantation site. The limiting mechanism 75 may include various configurations, e.g., a tapered portion, different shapes between the syringe body 10 and the dissection body 20, differently shaped protrusions, etc. The limiting mechanism 75 may be integrally formed with the syringe body 10 and the dissection body 20 (e.g., molded plastic) or may be added at a later time.

The end piece 43 is formed at a proximal end of the syringe body 10, for example, to provide an ergonomic configuration to the subcutaneous implantation tool 100. The end piece 43 may include various configurations, e.g., a syringe top, a circular ledge, etc., and may be integrally formed with the syringe body 10.

The micro-device 30 is a subcutaneous implantable device, e.g., medical device, etc. Exemplary embodiments include, various different types of implantable electronic devices, for example, sensors, transceivers, transmitters, receivers, both active and passive, powered, etc. The micro-device 30 may include various well known electronic components, e.g., memories, microprocessors, batteries, etc. Additional exemplary embodiments of the micro-device include, neuro-stimulators, acoustically powered sensors, pacers, etc. A current example is the REVEAL® Plus insertable loop recorder (ILR) used to automatically monitor a patient's heart. Depending on the type of electronic device and the method of manufacturing, the micro-device 30 may come in various shapes, e.g., rectangular, square, elongated, having blunt edges, having rounded edges, etc. and sizes, e.g., about 1 cubic centimeters (cc) to about 4 cc, etc.

Figure 3:
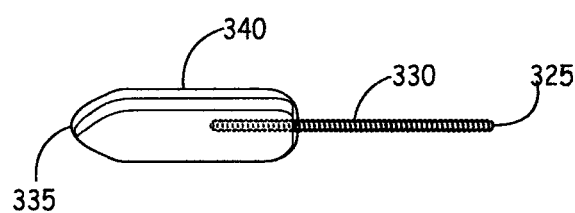

Exemplary embodiments of the micro-device 30 also include a "tailed" micro-device 30' (shown in FIG. 3). FIG. 3 illustrates an example embodiment of a micro-device 30' including a micro-device body 340 (including, e.g., a battery, electronics, memory, transmitter, etc.), a distal electrode 335, a tail 330 and a proximal electrode 325. The tail 330 may include at least one of the following: a lead, an electrode, an antenna, or other suitable element.

The tailed micro-device 30' allows for a required and/or desired minimum electrode spacing distance between the proximal electrode 325 and the distal electrode 335. Minimum electrode spacing depends on, e.g., the micro-device's implantation location and purpose and/or functionality. For example, if a minimum electrode spacing is 4 cm, a 1 cc device that would be long enough to accommodate this spacing may be so thin as to effect packaging efficiency and risk erosion due to pressure. By using the tailed micro-device 30', the minimum electrode spacing may be adjusted by adjusting the length of the tail 330.

Figure 5A:
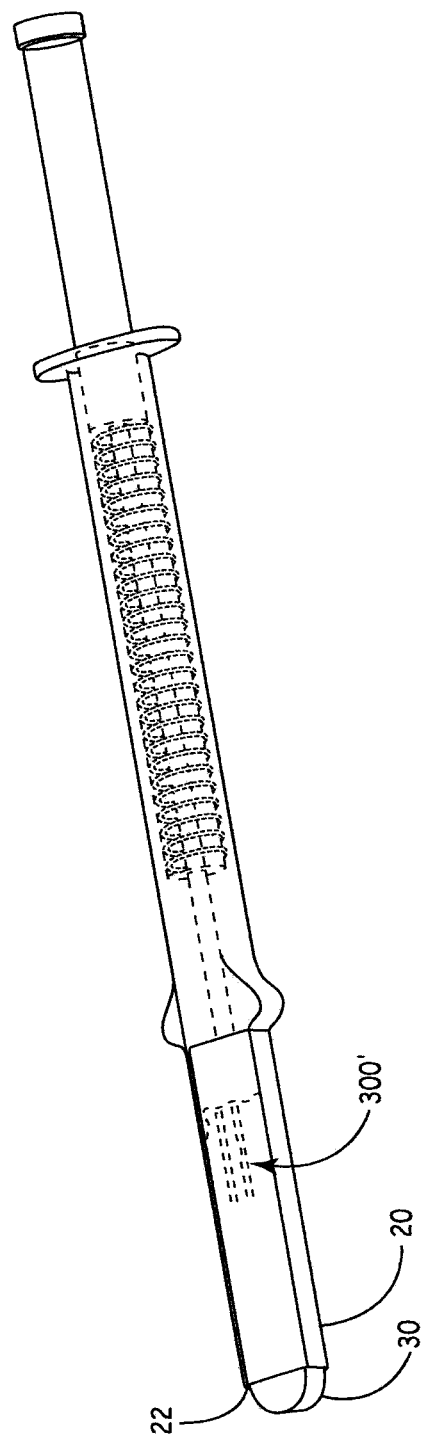
FIG. 5A and 5B illustrate exemplary embodiments of an implantation tool including a friction-fitted micro-device.
Figure 5B:
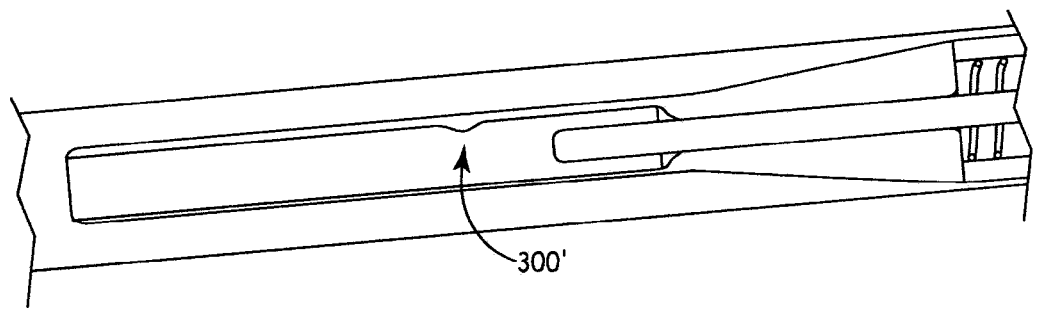

To ensure that a micro-device 30 remains seated in the subcutaneous implantation tool 100, exemplary embodiments may include a friction engagement feature. As shown in FIGS. 4A and 4B, a friction engagement feature 300 positively engages the micro-device 30 to prevent the micro-device 30 from falling out of the subcutaneous implantation tool 100 before successful implantation. The friction engagement feature 300 may have any shape that puts a relatively slight, positive pressure on the micro-device 30, but which pressure may be overcome by the sliding movement of the plunger 45. For example, as illustrated in FIGS. 4A and 4B, the friction engagement feature 300 is formed along a portion of the dissection body 20 as a relatively curved rectangular single piece spring. FIGS. 5A and 5B illustrate another example embodiment of a friction feature 300', formed along a portion of the dissection body 20 as a notch surrounded by two thin cutouts to form another type of spring. The friction engagement features 300 and 300' may be formed integrally with the dissection body 20.

Figure 6:
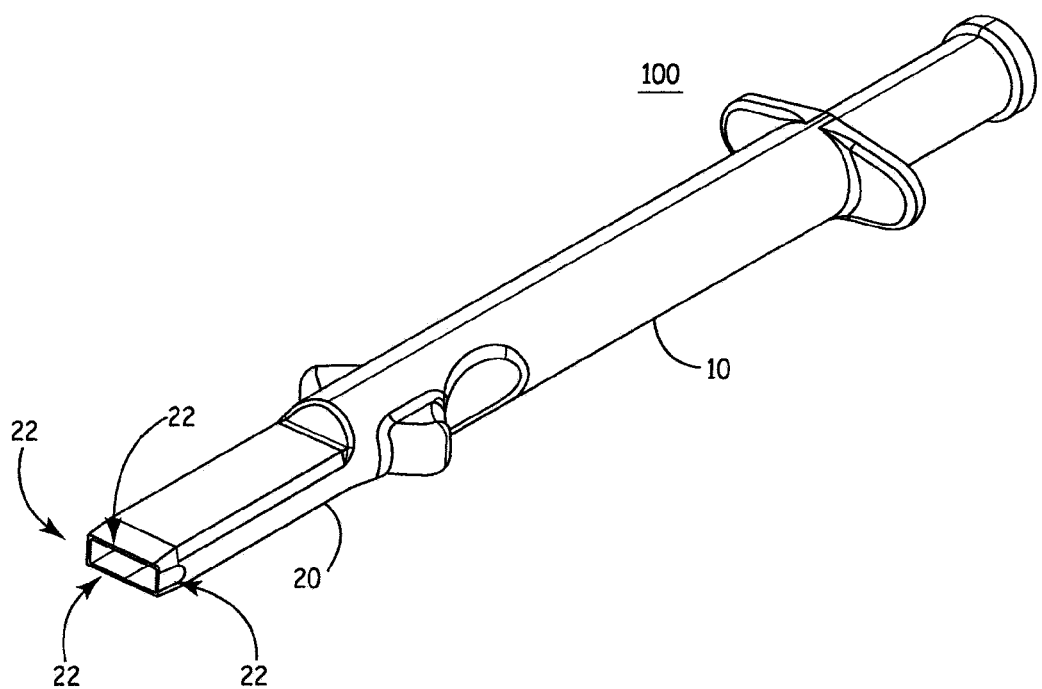

As shown in FIG. 6, the subcutaneous implantation tool 100 includes leading edges 22 at the distal end of the dissection body 20. The leading edges 22 are blunt as compared to sharp and allow the subcutaneous implantation tool 100 to utilize blunt dissection to form a subcutaneous pocket for the micro-device 30 during implantation. The pocket may be formed, for example, between the skin and fat layer or within the fat layer. Blunt dissection further allows increased control to prevent the micro-device 30 from being implanted into muscle, which has been associated with chronic pain. As discussed above, micro-device 30 may extend out from the distal end of the subcutaneous implantation tool 100. In this configuration, the micro-device may act to prevent the leading edges 22 of the subcutaneous implantation tool 100 from catching on tissue during implantation, e.g., when forming a pocket.

As shown in FIGS. 7A-7C, exemplary embodiments of the subcutaneous implantation tool 100 may include a sealed fluid reservoir 95 in at least a portion of the syringe body 10. The fluid reservoir 95 is sealed at a proximal end by a proximal seal 35 and at a distal end by a distal seal 37 thereby forming a watertight reservoir 95 between the seals. The seals 35 and 37 may be for example, o-rings, wiper seals, etc. The fluid reservoir 95 may be configured so that a majority of the fluid is located in an upper portion of the syringe body 10, for example, around the spring 90 and a proximal portion of the second portion 50 of plunger 45. For example, as shown in FIG. 7A-7C, the fluid reservoir 95 includes a proximal portion fit substantially around the spring 90 and within the syringe body 10, and a distal portion that narrows to surround a distal portion of the second portion 50 of plunger 45.

The fluid reservoir 95 may include fluids used to treat the incision site and/or the patient, e.g., antibiotics, anesthetizing agents, lubricants, saline, etc. When the plunger 45 is slid to deliver the micro-device 30, as described below, the distal seal 37 is moved and/or released into the dissection body 20, which is larger than the distal seal (see FIG. 7C), causing the fluid to flow through the subcutaneous implantation tool 100 and to be delivered to the implantation site with the micro-device 30.

Figure 8:
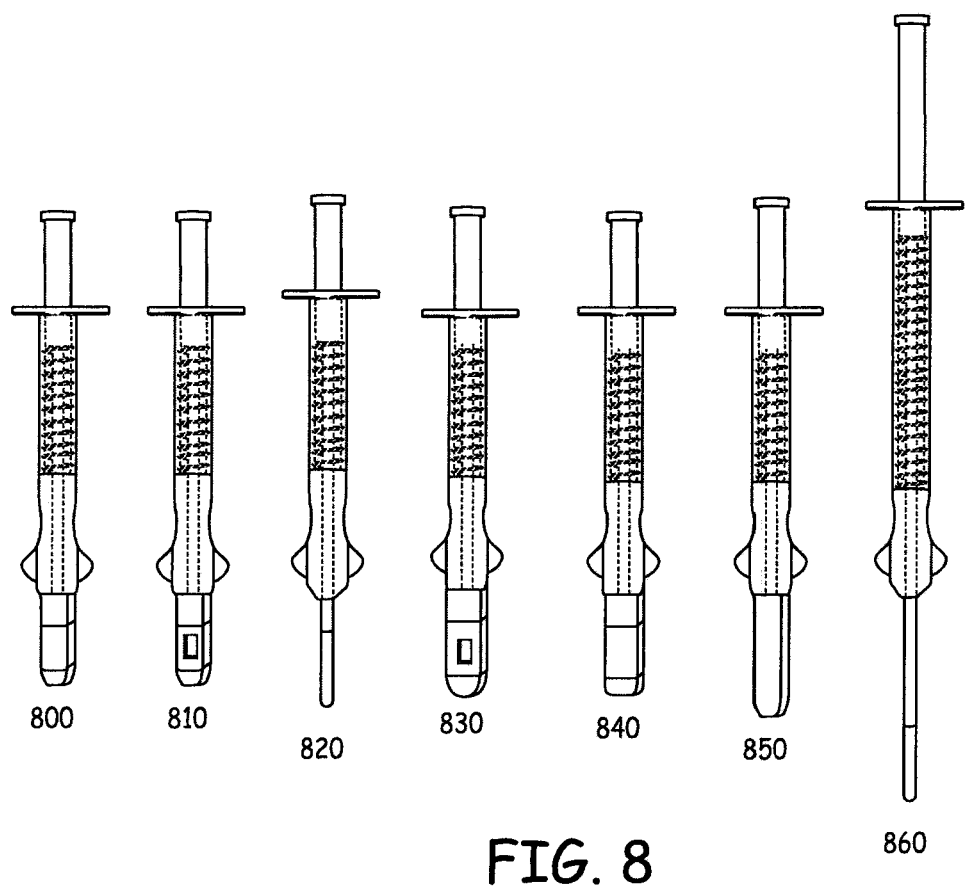

FIG. 8 illustrates exemplary embodiments of subcutaneous implantation tools 100 of various sizes and shapes (800 to 860). As shown, the various subcutaneous implantation tools 800-860 may be of different lengths, widths, and thicknesses. In addition, the area of the dissection body 20 in which a micro-device 30 is held may vary based on the size and shape of the micro-device 30. For example, the micro-device 30 may have a thickness ranging from about 0.01-0.5 inches, a width ranging from about 0.05-1.5 inches, and a length ranging from about 0.1-3 inches.

Exemplary embodiments also include methods of implanting a micro-device in a subcutaneous location. For example, a patient may undergo these types of procedures in a doctor's office, as an outpatient, or as an inpatient. The procedures may be performed in an office, at an outpatient location, or in a surgical operating suite.

Figure 9A:
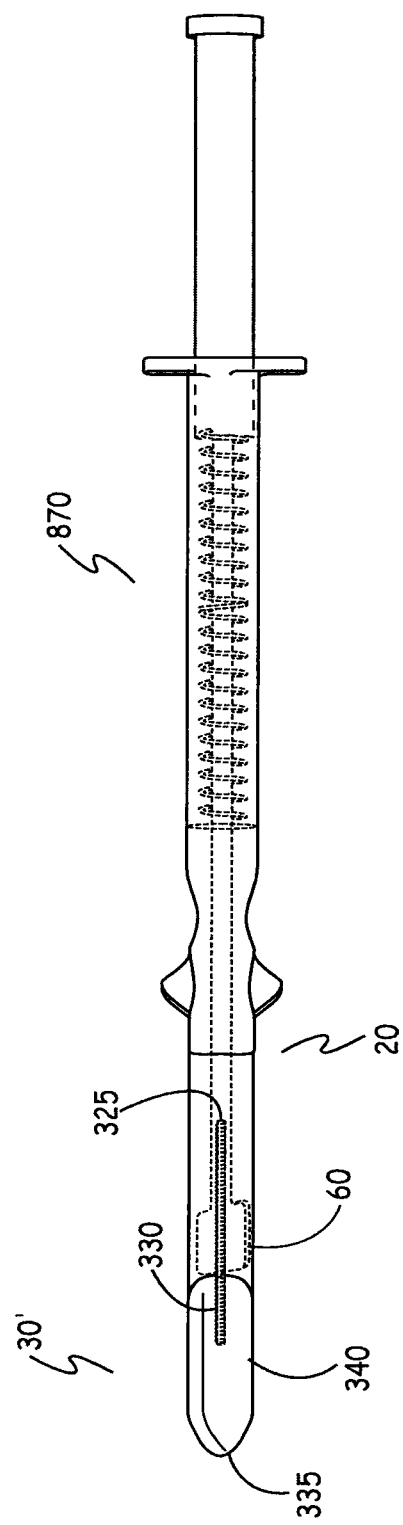
FIG. 9A-9F illustrate delivering a tailed micro-device.
Figure 9B:
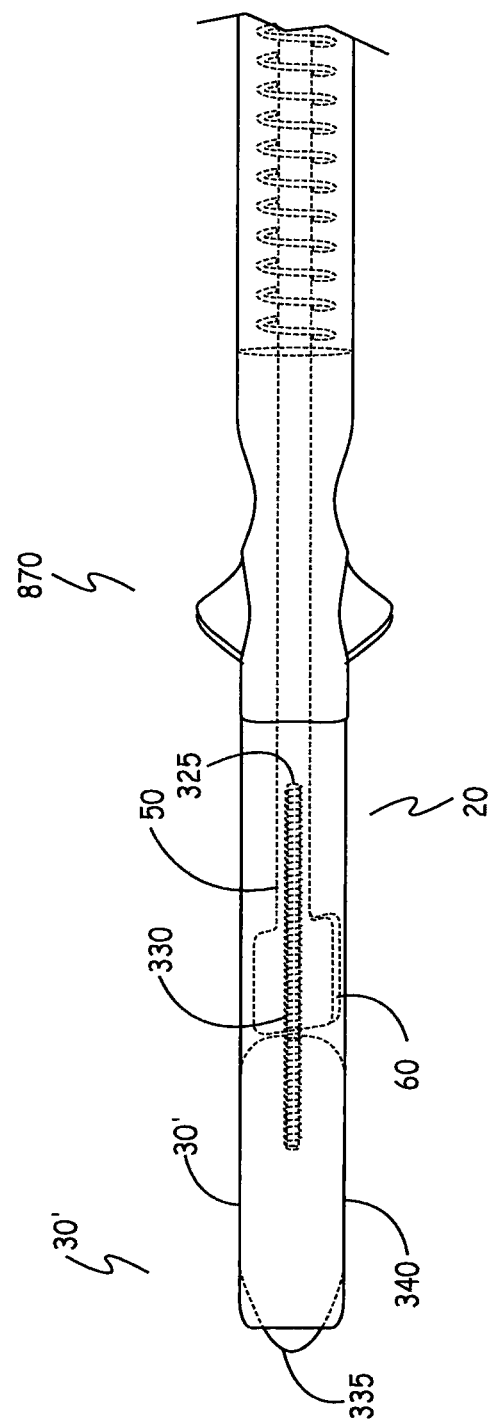

FIGS. 9A-9F show various views of exemplary embodiments of a subcutaneous implantation tool 870 including a tailed micro-device 30' in the process of delivering the tailed micro-device 30'. FIGS. 9A and 9B show a subcutaneous implantation tool 870 including a tailed micro-device 30' located in the distal end of the dissection body 20 and extending slightly there from. The tailed micro-device 30' includes a device body 340 including a distal electrode 335 and a proximal electrode 325, which is part of the tail 330. The tail 330 is shown as extending from within the device body 340 through end piece 60 and into second portion 50 of plunger 45 along a longitudinal axis. It is noted that this is but one example of how the tailed micro-device 30' may be held by subcutaneous implantation tool 870 and is not intended to be limiting.

Figure 9C:
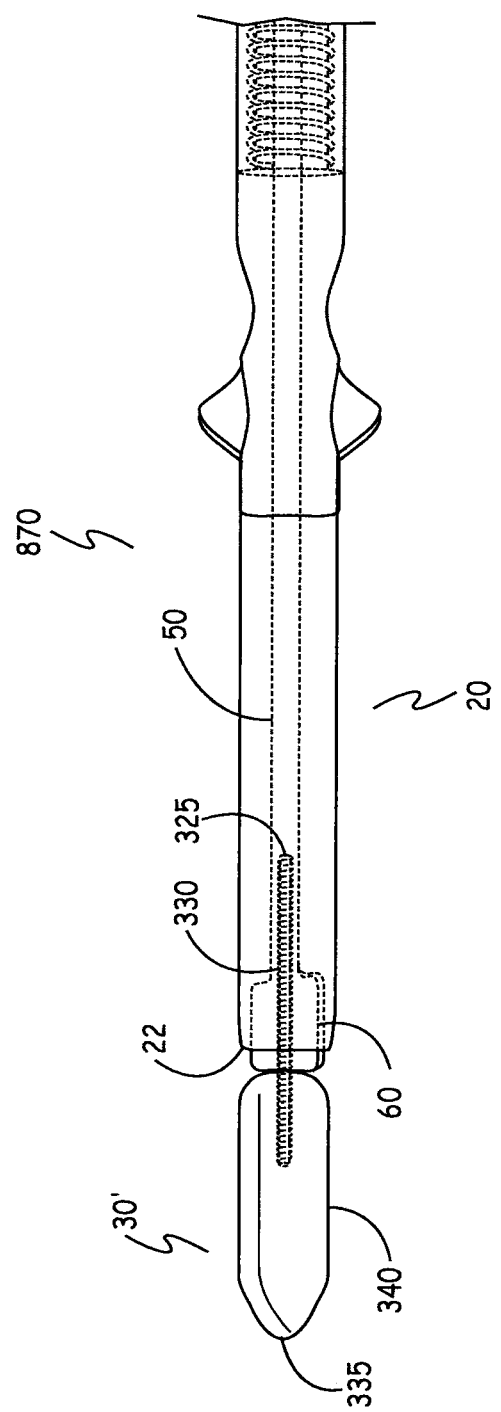
Figure 9D:
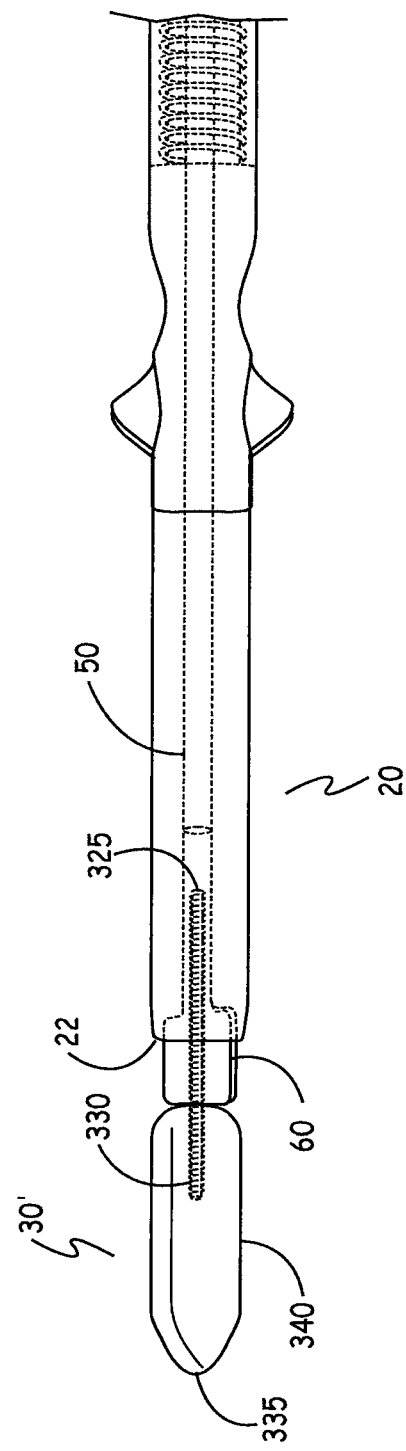
Figure 9E:
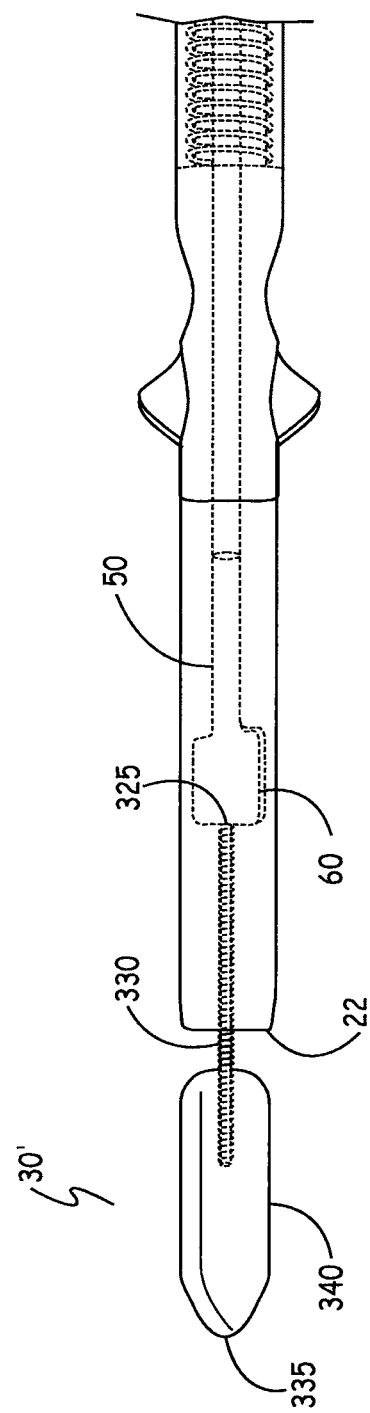
Figure 9F:
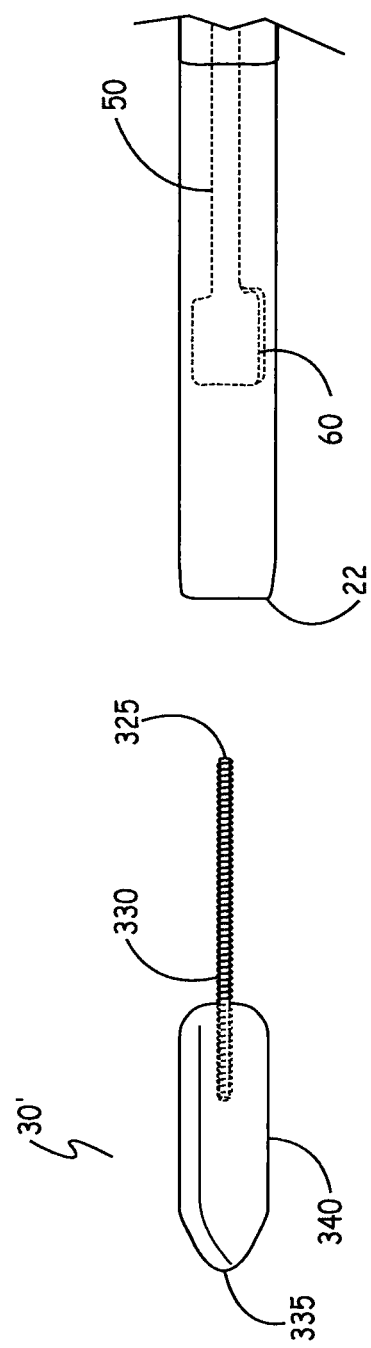

FIGS. 9C and 9D show micro-device 30' being pushed out of dissection body 20 by end piece 60 and plunger 45 but still attached to end piece 60 and plunger 45. In FIG. 9D, end piece 60 continues to extend beyond the leading edges 22 of dissection body 20. FIG. 9E shows the plunger 45 of subcutaneous implantation tool 870 beginning to be released so that the tail 330 of micro-device 30' is withdrawn from end piece 60 and second portion 50 of plunger 45. FIG. 9F shows micro-device 30' having been delivered and the subcutaneous implantation tool 870 being removed following implantation.

While the above steps and views illustrated the delivery of a tailed micro-device 30', similar steps may be used to deliver any type of micro-device. Also, the configuration of a micro-device 30 may be adjusted to ensure that the micro-device 30 does not become loose in the subcutaneous implantation tool 100 until delivery is desired. For example, the tailed micro-device 30' as shown in FIGS. 9A-9F had the tail 330 extending through end piece 60 and second portion 50 of plunger 45, but the tail 330 may extend only through end piece 60, etc. Further, as discussed above, a micro-device 30 may be fitted in dissection body 20 using a friction feature, etc.

Figure 10:
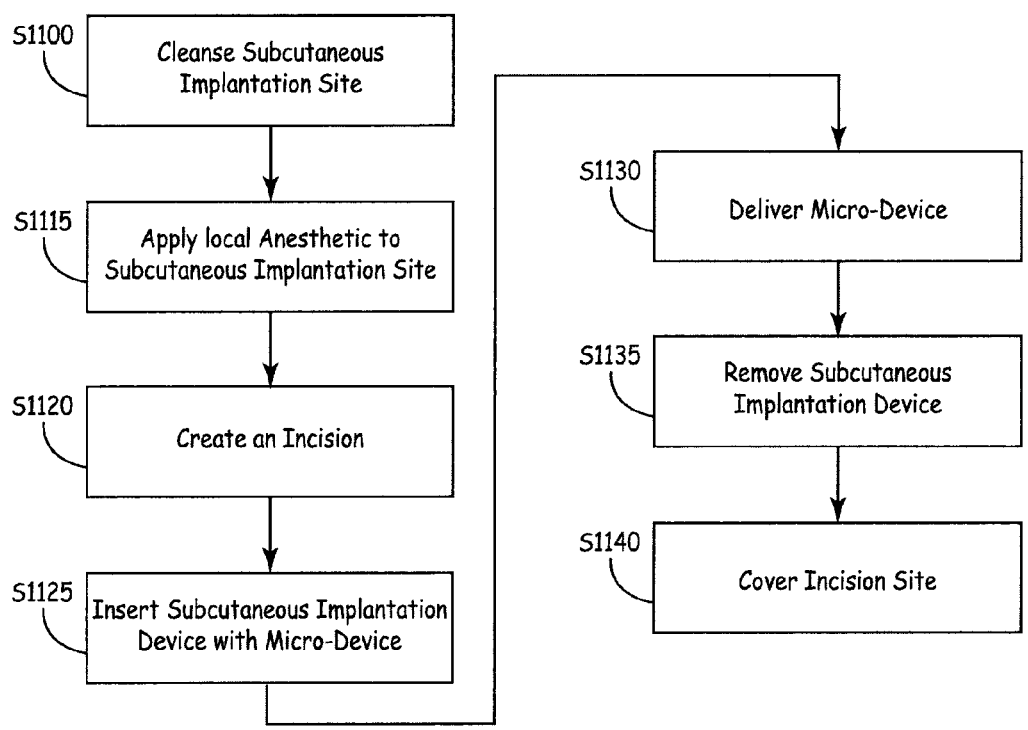

Following a determination that a patient would benefit from and/or needs a micro-device 30 implanted subcutaneously, an example embodiment of the method shown in FIG. 10 may be used. Initially, the subcutaneous implantation site should be cleansed in step S1110 and a local anesthetic applied in step S1115. If the procedure is being performed as part of a surgery, then general anesthesia may be used. Next an incision in step S1120 is made at the subcutaneous implantation site. The incision may be made with a separate instrument or device, e.g., a scalpel, scissors, etc. After an incision is made, the subcutaneous implantation tool 100 is inserted into the incision site in step S1125. After insertion, the micro-device 30 is delivered in step S1130 and the subcutaneous implantation tool 100 is removed in step S1135. Finally, the incision site should be covered as shown in step S1140.

Exemplary embodiments also include numerous variations of the above described method. For example, during step S1125, the dissection body 20 including a micro-device 30, may be the only part of the subcutaneous implantation tool 100 inserted into the incision site. By only inserting the dissection body 20, a smaller incision will likely be needed in step S1120 and the penetration distance under the dermal layer in step S1130 may be reduced. Exemplary embodiments also include using the subcutaneous implantation tool 100 and/or the dissection body 20, to create a pocket between the dermal layer and the subcutaneous layer by adjusting the inserted portion in step S1125. By creating a pocket, the delivery of the micro-device 30 in step S1130 is easier and one is less likely to deliver the micro-device 30 into muscle. In addition, if the subcutaneous implantation tool 100 includes a fluid reservoir 95 as described above, the fluid stored therein may be delivered to the implantation site during step S1130.

Exemplary embodiments thus described allow for subcutaneous implantation of micro-devices that are minimally invasive. Note that exemplary embodiments may be used in both human and animal patients.

Exemplary embodiments of the present invention being thus described, it will be obvious that the same may be varied in many ways. Such variations are not to be regarded as a departure from the spirit and scope of the exemplary embodiments of the invention, and all such modifications as would be obvious to one skilled in the art are intended to be included within the scope of the invention.

What is claimed is:

1. A subcutaneous implantation tool comprising:
    a syringe body having a hollow bore of a first shape extending along a longitudinal axis;
    a dissection body at a distal end of the syringe body having a substantially non-circular hollow bore having a second shape different than the first shape extending along the longitudinal axis and configured to receive a subcutaneous implantation micro-device, wherein the hollow bore is substantially non-circular at a distal end of the tool; and
    a delivery assembly including a plunger fitting within at least a portion of the syringe body bore and a first end piece attached to a distal end of the plunger, the plunger including first and second portions, the second portion attached to a distal end of the first portion, wherein at least a portion of the first portion fits within the hollow bore of the syringe body and the second portion being narrower than the first portion and the first end piece.

2. The tool of claim 1, wherein the first end piece fits into at least a portion of the dissection body.

3. The tool of claim 2, wherein the plunger being slidably fitted within at least the portion of the syringe body and at least the portion of the dissection body.

4. The tool of claim 1, wherein the delivery assembly being configured to facilitate deployment of the subcutaneous implantation micro-device.

5. The tool of claim 1, wherein the plunger includes a second end piece at a proximal end of the first portion, located outside of the syringe body, wherein the end piece being configured to stop the syringe body from moving along the longitudinal axis.

6. The tool of claim 1, further including:
    a penetration limiting mechanism at the distal end of the syringe body.

7. The tool of claim 1, wherein the distal end of the tool has blunt edges.

8. The tool of claim 7, wherein a distal end of the dissection body has blunt edges.

9. The tool of claim 1, further including:
    a subcutaneous implantation micro-device wherein the micro-device extends beyond
    a distal end of the dissection body and wherein the micro-device being an implantable medical device.

10. The tool of claim 9, wherein the micro-device includes at least one of the following: a sensor, a transceiver, a transmitter, a receiver, a pacer, a neuro-stimulator, and an acoustically powered sensor.

11. The tool of claim 1, further including:
    a spring attached to the distal end of the plunger's first portion and fitted within the syringe body.

12. The tool of claim 11, wherein the spring surrounds at least a portion of the plunger's second portion.

13. The tool of claim 1, wherein the tool elements are each formed from at least one of the following: sanitizable plastic, sanitizable metal, sanitizable rubber, and medical grade materials.

14. The tool of claim 1, further including:
    a fluid reservoir conformably fit within at least a portion of the syringe body.

15. The tool of claim 14, wherein the fluid reservoir includes a proximal seal and a distal seal.

16. The tool of claim 14, wherein the fluid reservoir being configured to hold liquid including at least one of the following: antibiotics, saline, lubricants, and anesthetizing agents.

17. The tool of claim 14, further including:
a micro-device extending from the dissection body, wherein the micro-device being an implantable medical device.

18. The tool of claim 14, wherein the micro-device being at least one of the following: a sensor, a transceiver, a transmitter, a receiver, a pacer, a neuro-stimulator, and an acoustically powered sensor.

19. The tool of claim 1, wherein the end piece being configured to deploy a tailed micro-device.

20. A subcutaneous implantation tool comprising:
a syringe body having a hollow bore of a first shape extending along a longitudinal axis;
a dissection body at a distal end of the syringe body having a substantially non-circular hollow bore having a second shape different than the first shape extending along the longitudinal axis and configured to receive a subcutaneous implantation micro-device;
a fluid reservoir conformably fit within at least a portion of the syringe body between a proximal seal and a distal seal; and
a delivery assembly including a plunger fitting within at least a portion of the syringe body bore and a first end piece attached to a distal end of the plunger, the plunger including first and second portions, the second portion attached to a distal end of the first portion and the second portion being narrower than the first portion;
wherein movement of the plunger towards the dissection body opens the distal seal of the fluid reservoir such that fluid in the fluid reservoir can flow through the dissection body.

21. The tool of claim 20, wherein the proximal seal seals the fluid reservoir at the distal end of the first portion of the plunger and the distal seal seals the fluid reservoir at a distal end of the second portion of the plunger.

22. The tool of claim 20, wherein the fluid reservoir being configured to hold liquid including at least one of antibiotics, saline, lubricants, and anesthetizing agents.

23. The tool of claim 20, further including a subcutaneous implantation micro-device fit into at least a portion of the dissection body wherein the micro-device extends beyond a distal end of the dissection body.

24. A subcutaneous implantation tool comprising:
a syringe body including a hollow bore of a first shape extending along a longitudinal axis;
a spring fitted within the syringe body;
a dissection body at a distal end of the syringe body having a substantially non-circular hollow bore having a second shape different than the first shape extending along the longitudinal axis and configured to receive a subcutaneous implantation micro-device, wherein the hollow bore is substantially non-circular at a distal end of the tool; and
a delivery assembly including a plunger fitting within at least a portion of the syringe body bore and a first end piece attached to a distal end of the plunger, the plunger including first and second portions, the second portion attached to a distal end of the first portion wherein the second portion being narrower than the first portion and the first end piece.

25. A subcutaneous implantation tool comprising:
a syringe body having a hollow bore of a first shape extending along a longitudinal axis;
a dissection body at a distal end of the syringe body having a substantially non-circular hollow bore having a second shape different than the first shape extending along the longitudinal axis and configured to receive a subcutaneous implantation micro-device, wherein the hollow bore is substantially non-circular at a distal end of the tool;
a delivery assembly including a plunger fitting within at least a portion of the syringe body bore and a first end piece attached to a distal end of the plunger, the plunger including first and second portions, and the second portion attached to a distal end of the first portion wherein the second portion being narrower than the first portion and the first end piece; and
a subcutaneous implantation micro-device frictionally fit into at least a portion of the dissection body.

26. The tool of claim 25, wherein the micro-device extends beyond a distal end of the dissection body.

27. The tool of claim 25, wherein the micro-device being at least one of the following: a sensor, a transceiver, a transmitter, and a receiver.

28. The tool of claim 25, wherein the end piece being configured to deploy a tailed micro-device.

29. A method for implanting a micro-device in a subcutaneous location, comprising:
inserting the dissection body of the tool of claim 1 into an implantation site, wherein the dissection body includes a micro-device; and
delivering the micro-device.

30. The method of claim 29, further including:
adjusting the dissection body to form a pocket at the implantation site.

31. The method of claim 29, wherein the delivering step includes sliding the syringe body towards a proximal end of the plunger.

32. The method of claim 30, further including:
delivering a fluid.

33. The method of claim 30, further including:
limiting the insertion of the tool by a limiting mechanism.

34. The method of claim 33, wherein the limiting mechanism includes at least a change in shape between the syringe body and the dissection body.

35. A method for implanting a micro-device in a subcutaneous location, comprising:
inserting the dissection body of the tool of claim 20 into an implantation site, wherein the dissection body includes a micro-device;
limiting insertion of the dissection body;
adjusting the dissection body to form a pocket at the implantation site; and
delivering the micro-device and a fluid into the pocket.

36. The tool of claim 19, wherein the end piece is configured to receive a tail of the micro-device extending through the end piece to retain the micro-device within the dissection body until delivery of the micro-device at an implantation site.

* * * * *